(12) United States Patent
Nishijima et al.

(10) Patent No.: US 9,791,366 B2
(45) Date of Patent: Oct. 17, 2017

(54) GAS DETECTOR, GAS DETECTION METHOD AND OPTICAL COMPONENT

(71) Applicant: National University Corporation Yokohama National University, Yokohama, Kanagawa (JP)

(72) Inventors: Yoshiaki Nishijima, Yokohama (JP); Yuta Adachi, Yokohama (JP)

(73) Assignee: NATIONAL UNIVERSITY CORPORATION YOKOHAM NATIONAL UNIVERSITY (JP)

( * ) Notice: Subject to any disclaimer, the term of this patent is extended or adjusted under 35 U.S.C. 154(b) by 0 days.

(21) Appl. No.: 14/784,548

(22) PCT Filed: Apr. 8, 2014

(86) PCT No.: PCT/JP2014/060299
§ 371 (c)(1),
(2) Date: Oct. 14, 2015

(87) PCT Pub. No.: WO2014/171372
PCT Pub. Date: Oct. 23, 2014

(65) Prior Publication Data
US 2016/0054220 A1    Feb. 25, 2016

(30) Foreign Application Priority Data

Apr. 18, 2013 (JP) ................. 2013-087683

(51) Int. Cl.
*G01N 21/3504* (2014.01)
*G01N 21/359* (2014.01)
*G01N 21/552* (2014.01)

(52) U.S. Cl.
CPC ....... *G01N 21/3504* (2013.01); *G01N 21/359* (2013.01); *G01N 21/553* (2013.01);
(Continued)

(58) Field of Classification Search
CPC .... G01J 3/51; G01J 5/08; G01J 5/0862; G01J 5/20; G01N 21/3504; H01L 27/14618; H01L 27/14649; H01L 2924/0002
See application file for complete search history.

(56) References Cited

U.S. PATENT DOCUMENTS

2003/0023181 A1* 1/2003 Mault ................. A61B 5/0833
                                                        600/532
2004/0211901 A1* 10/2004 Syllaios ................. G01J 3/51
                                                        250/339.02
(Continued)

FOREIGN PATENT DOCUMENTS

JP        6102184 A      4/1994
JP        2006524338 A   10/2006
(Continued)

OTHER PUBLICATIONS

Nslishijima, et al., "Selective Enhancement of Infrared Absorption with Metal Hold Arrays," Opt. Mater. Express, Sep. 7, 2012, pp. 1367-1377, XP055329236.*
(Continued)

*Primary Examiner* — Luke Ratcliffe
(74) *Attorney, Agent, or Firm* — Burns & Levinson LLP; Joseph M. Maraia

(57) ABSTRACT

A gas detector (10) includes a cell internal space (130) into which a target gas is supplied, the target gas exhibiting an absorption peak in an absorption spectrum; a light source (410) configured to generate light having at least a wavelength belonging to the absorption peak; and a photodetector (420) configured to detect the light that has emitted from the light source (410) and has propagated through the cell internal space (130). The gas detector (10) further includes a conductive thin film (220) in which a plurality of optical apertures (222) are regularly arranged such that a transmission peak in a transmission spectrum is superimposed over
(Continued)

the absorption peak in the absorption spectrum along a wavelength axis. The conductive thin film (220) is provided on an optical path extending from the light source (410) to the photodetector (420), and is provided so as to be contactable with the target gas within the cell internal space (130).

9 Claims, 15 Drawing Sheets

(52) U.S. Cl.
CPC ..... *G01N 21/554* (2013.01); *G01N 2201/061* (2013.01); *G01N 2201/0635* (2013.01)

(56) References Cited

U.S. PATENT DOCUMENTS

| 2005/0173635 | A1  | 8/2005 | Smith |
|---|---|---|---|
| 2006/0044562 | A1* | 3/2006 | Hagene .................. G01N 21/39 356/437 |
| 2010/0178713 | A1  | 7/2010 | Nishiuma et al. |
| 2012/0113424 | A1  | 5/2012 | Suda et al. |
| 2012/0190997 | A1  | 7/2012 | Varga |

FOREIGN PATENT DOCUMENTS

| JP | 2007218900 A | 8/2007 |
|---|---|---|
| JP | 2010139299 A | 6/2010 |
| JP | 201153151 A | 3/2011 |
| JP | 201273226 A | 4/2012 |

OTHER PUBLICATIONS

International Preliminary Report for related International Application No. PCT/JP2014/060229 mailed Oct. 22, 2015.

Nishijima, et al., "Selective Enhancement of Infrared Absorption with Metal Hold Arrays," Opt. Mater. Express, Sep. 7, 2012, pp. 1367-1377, XP055329236.

European Search Report from related European Application No. 14784955.8-1554 dated Jan. 3, 2017.

* cited by examiner (a)

(b)

GAS DETECTOR, GAS DETECTION METHOD AND OPTICAL COMPONENT

CROSS REFERENCE TO RELATED APPLICATIONS

This application is a U.S. national stage application under 35 U.S.C. 371 of co-pending International Application No. PCT/JP/2014/060229, filed on Apr. 8, 2014. The International Application, in turn, claims priority to Japanese Patent Applications No. 2013-087683, filed on Apr. 18, 2013. The entire contents of the above applications are incorporated herein by reference for all purposes.

TECHNICAL FIELD

The present disclosure relates to a gas detector, a gas detection method and an optical component.

BACKGROUND

Gas detectors are utilized in various fields, such as in the fields of medical treatments, environmental measurements and various kinds of testing. Gas detectors are utilized, for example, to detect exhaust gas of air conditioners, exhaust gas of automobiles, exhaust gas from factories, leaking gas in domestic households, toxic gases such as gases associated with sick house syndrome, and odorous gas of raw garbage and pets and the like.

Examples of gas detection methods include semiconductor type detection, contact combustion type detection, thermal conductivity type detection, and NDIR (non-dispersive infrared) type detection. The semiconductor type detection detects changes in electrical resistance caused by gas that is exposed to a semiconductor, and although this type of detection offers the advantages of being compact and having a high degree of mass productivity, there is the drawback that the semiconductor type detection lacks stability. The contact combustion type detection combusts gas inside an apparatus, and is limited to combustible gases. The thermal conductivity type detection detects a temperature change that is in accordance with a difference in the thermal conductivity of a gas, and has the drawback of low sensitivity. The NDIR type detection has an advantage of being applicable to various kinds of gases, having high sensitivity and providing long-term operational stability. However, there is a drawback that the apparatus size may be larger as sufficient optical path length is required.

Patent Literature 1 discloses, in its abstract, that, in order to keep the intensity of output light from an infrared light source 8 constant, an infrared detector 9B detects infrared light passing through an optical filter 10 B and having a wavelength that is not absorbed by gas, and controls an applied voltage to the infrared light source 8.

CITATION LIST

Patent Literature

Patent Literature 1:Japanese Patent Laid-Open No. 2010-139299

SUMMARY

Technical Problem

For a method for measuring a target gas concentration in accordance with attenuation of light, typically the NDIR method, there is an inherent drawback that securing a long optical path length is required to improve the detection sensitivity.

Solution to Problem

A gas detector according to an aspect of the present invention may include a space into which a target gas is supplied, the target gas exhibiting an absorption peak in an absorption spectrum; a light source configured to generate light having at least a wavelength belonging to the absorption peak; and a photodetector configured to detect the light that has emitted from the light source and has propagated through the space, wherein the gas detector may further include a conductive thin film in which a plurality of optical apertures are regularly arranged such that a transmission peak in a transmission spectrum is superimposed over the absorption peak in the absorption spectrum along a wavelength axis, and wherein the conductive thin film is provided on an optical path extending from the light source to the photodetector, and is provided so as to be contactable with the target gas within the space.

In some embodiments, the plurality of optical apertures are two-dimensionally arranged at a predetermined interval along first and second directions that are orthogonal one another in a plane where the conductive thin film exists.

In some embodiments, the plurality of optical apertures include a first and second optical aperture arrays in which the optical apertures are arranged along the first direction, the second optical aperture array being arranged adjacent to the first optical aperture array in the second direction, and arrangement positions of the optical apertures in the second optical aperture array being shifted in the first direction by an amount corresponding to a value of half of the predetermined interval relative to arrangement positions of the optical apertures in the first optical aperture array.

In some embodiments, an interval between the adjacent optical apertures in the optical aperture array in which the optical apertures are arranged along the first direction and an interval between the optical aperture in said optical aperture array and the optical aperture in another optical aperture array adjacent thereto in a diagonal direction are equal.

In some embodiments, the plurality of optical apertures are respectively provided at positions each corresponding to a vertex in a triangular shape that is a unit of a triangular lattice.

In some embodiments, the conductive thin film is provided on a support substrate that is transparent to the emitted light from the light source.

In some embodiments, the support substrate on which the conductive thin film is provided is a window member that intermediates propagation of the emitted light from the light source to the space, or that intermediates propagation of the light that has propagated through the space to the photodetector.

In some embodiments, the conductive thin film is selected from a group consisting of silver, gold, copper, chromium, aluminum, iron, titanium, nickel, cobalt, rhodium, palladium, platinum, iridium, ruthenium, osmium, zinc, and rhenium.

In some embodiments, the space is defined by a gas cell having a gas inlet and a gas outlet.

In some embodiments, the space is defined by a gas cell having a gas inlet and a gas outlet, and the conductive thin film is provided on a reflective inner side of the gas cell.

In some embodiments, the space is defined by a reflective spherical surface, and the conductive thin film is provided on the spherical surface.

An optical component according to another aspect of the present invention may include a support substrate that is transparent to light having a wavelength belonging to an absorption peak of a target gas that exhibits the absorption peak in an absorption spectrum; and a conductive thin film that is provided on the support substrate, a plurality of optical apertures are regularly arranged such that a transmission peak in a transmission spectrum is superimposed over the absorption peak in the absorption spectrum along a wavelength axis.

In some embodiment, in a case where the plurality of optical apertures are two-dimensionally arranged at a predetermined interval along first and second directions that are orthogonal one another in a plane where the conductive thin film exists, the plurality of optical apertures include first and second optical aperture arrays in which the optical apertures are arranged along the first direction, the second optical aperture array being arranged adjacent to the first optical aperture array in the second direction, and arrangement positions of the optical apertures in the second optical aperture array being shifted in the first direction by an amount corresponding to a value of half of the predetermined interval relative to arrangement positions of the optical apertures in the first optical aperture array.

A gas detection method according to still another aspect of the present invention may include: irradiating, to a conductive thin film provided in a space to which a target gas having an absorption peak in an absorption spectrum is supplied, light having at least a wavelength belonging to the absorption peak, wherein a plurality of optical apertures is regularly arranged in the conductive thin film such that a transmission peak in a transmission spectrum is superimposed over the absorption peak in the absorption spectrum along a wavelength axis; and detecting the light that has propagated through the space via the conductive thin film.

Advantageous Effect

According to one aspect of the present invention it may be possible to secure sufficient gas detection sensitivity without greatly depending on an optical path length inside an apparatus.

DESCRIPTION OF EMBODIMENTS

Hereunder, embodiments of the present invention will be described with reference to the accompanying drawings. The respective embodiments are not individually independent and may be suitably combined by those skilled in the art without providing excessive descriptions herein, and a synergistic effect resulting from such a combination may also be recognizable. In principle, duplicate descriptions among the embodiments shall be omitted.

[First Embodiment]

Figure 1:
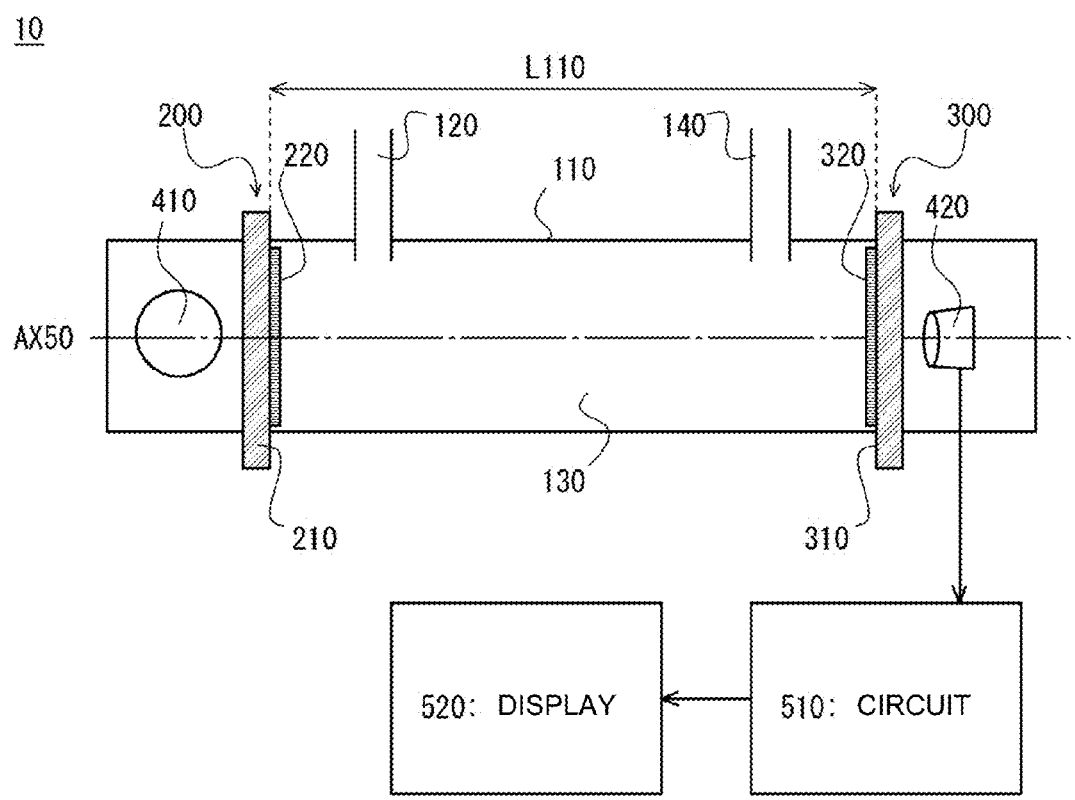
FIG. 1 is a schematic diagram illustrating a schematic cross-sectional configuration of a gas detector according to a first embodiment of the present invention.
Figure 2:
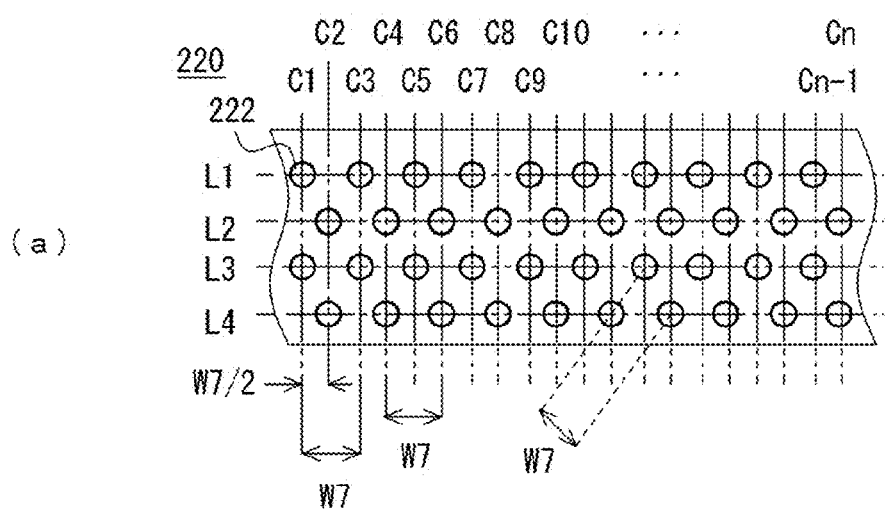
FIG. 2 is a schematic diagram illustrating the schematic configuration of a window member incorporated into the gas detector according to the first embodiment of the present invention, (a) illustrating a partial and schematic upper surface configuration of the window member, and (b) illustrating a schematic cross-sectional configuration of the window member.
Figure 2:
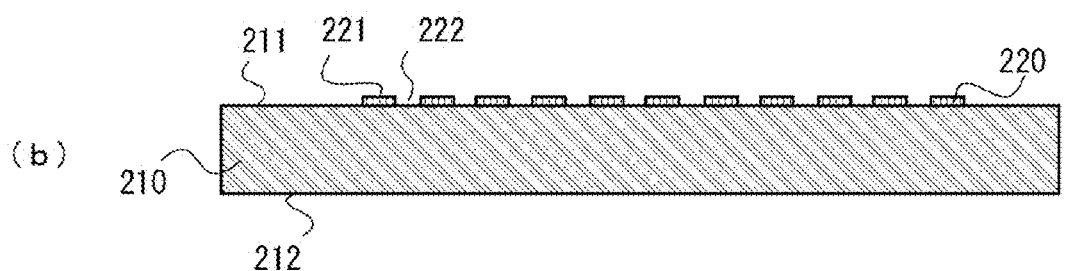
Figure 3:
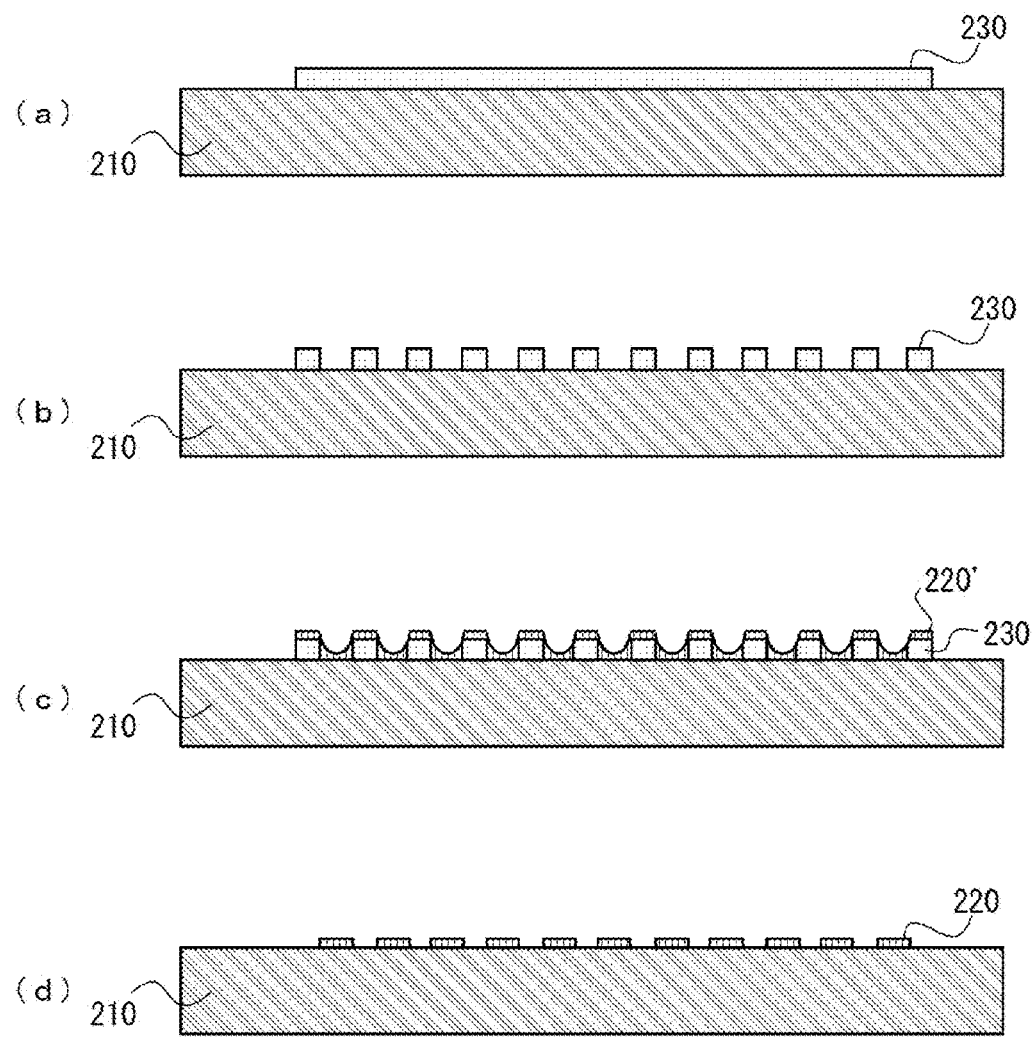
FIG. 3 is a process diagram illustrating a method for manufacturing the window member incorporated into the gas detector according to the first embodiment of the present invention.
Figure 4:
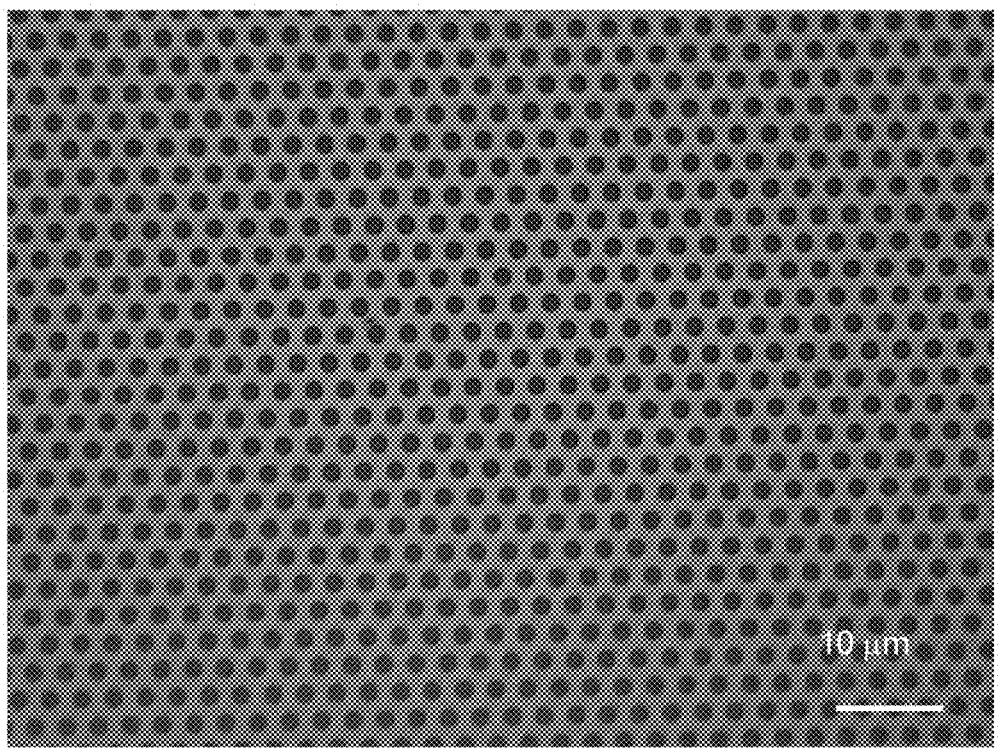
FIG. 4 is a photograph showing the upper surface of the window member incorporated into the gas detector according to the first embodiment of the present invention.
Figure 5:
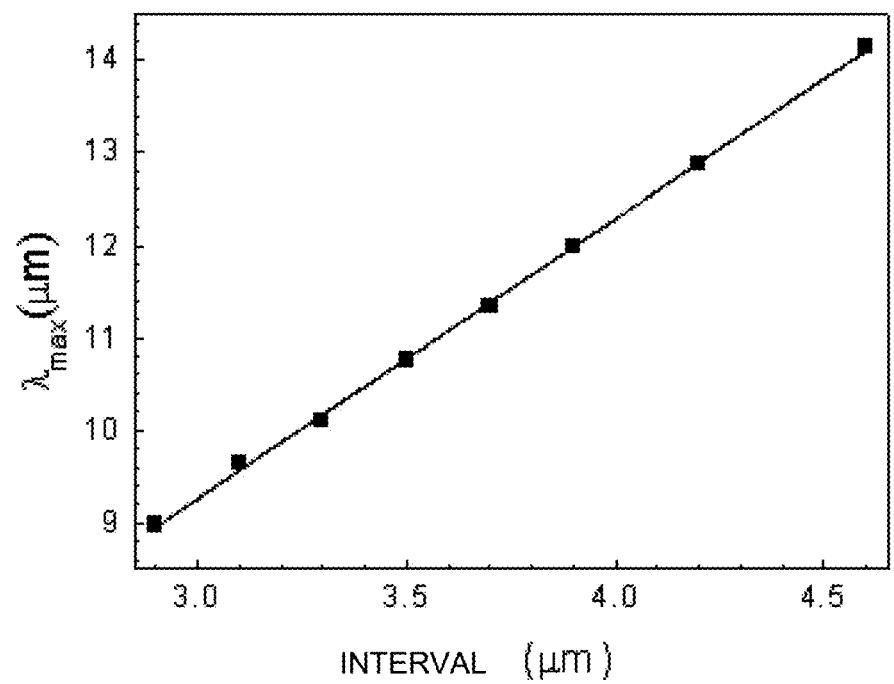
FIG. 5 is a graph illustrating the relation between an interval between optical apertures of an conductive thin film of the window member incorporated into the gas detector according to the first embodiment of the present invention and a wavelength ($\lambda_{m\,a\,x}$) of the maximum transmittance at a transmission peak in a transmission spectrum.
Figure 6:
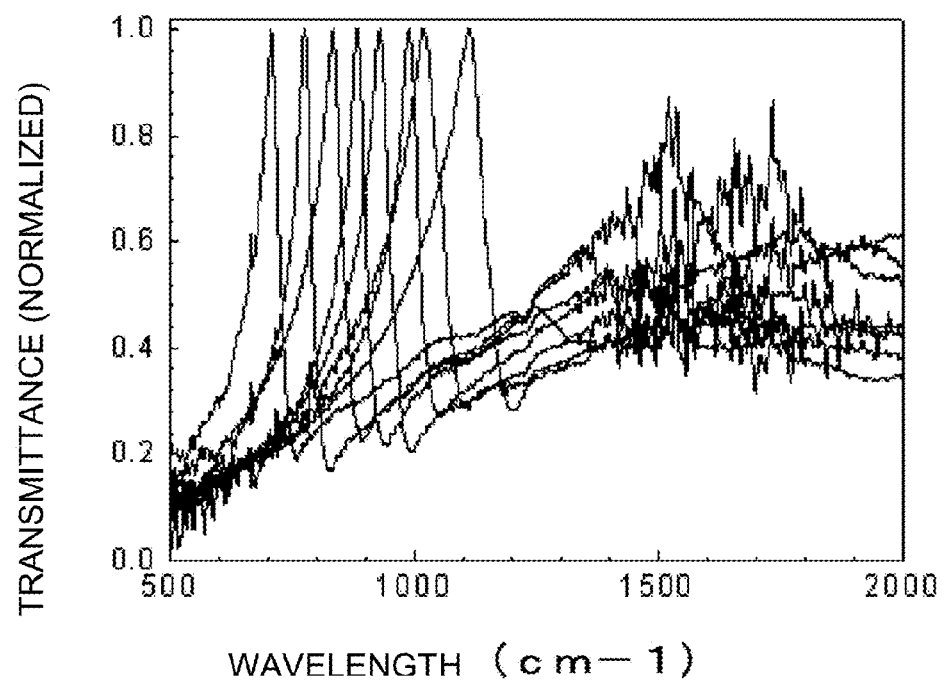
FIG. 6 is a graph illustrating a comparison between transmission spectra of respective conductive thin films for the window member incorporated into the gas detector according to the first embodiment of the present invention.
Figure 7A:
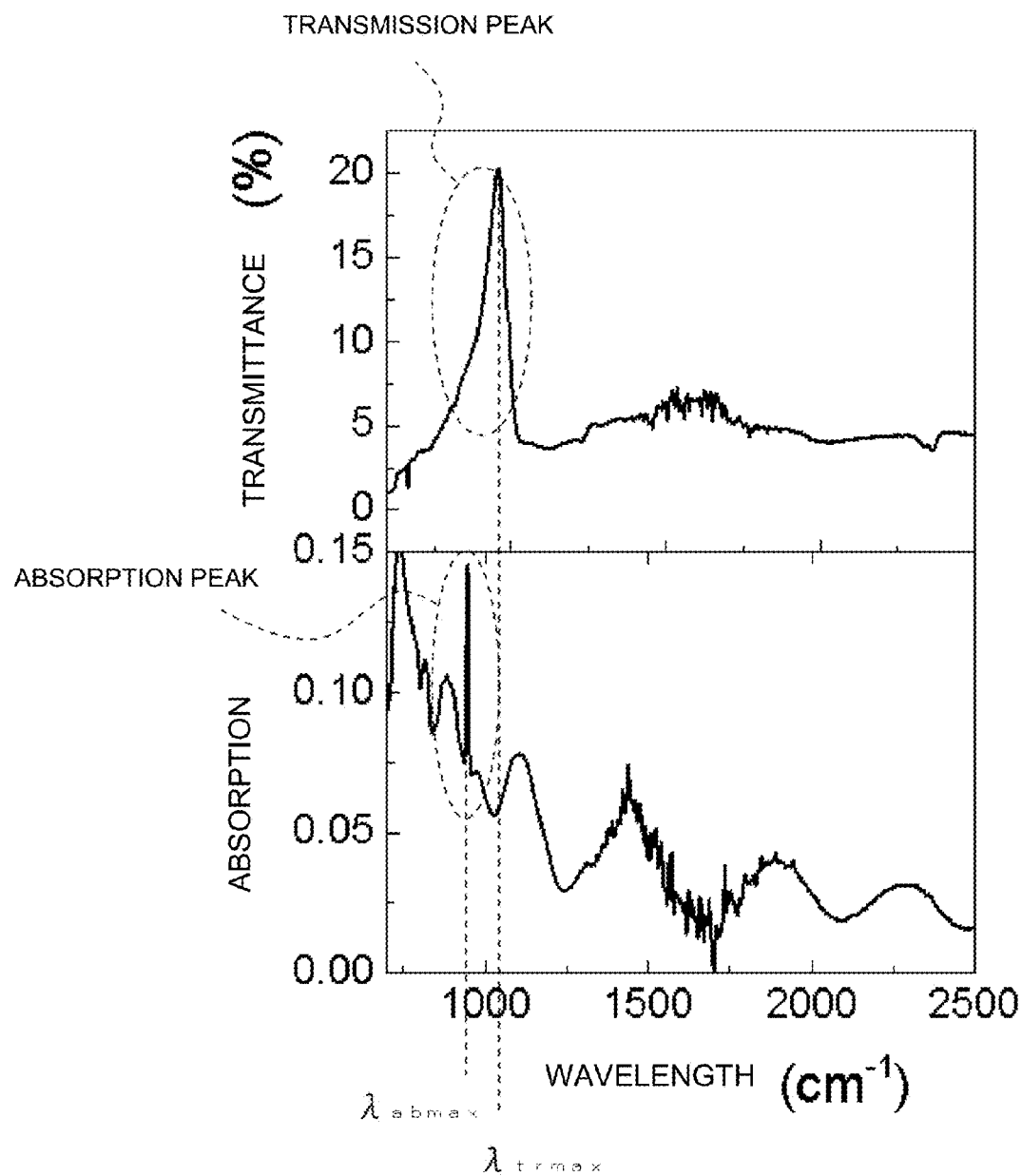
FIG. 7A is a graph illustrating a transmission spectrum of the conductive thin film of the window member incorporated into the gas detector according to the first embodiment of the present invention and an absorption spectrum of a target gas along the same wavelength axis, showing that the transmission spectrum and the absorption spectrum are superimposed.
Figure 7B:
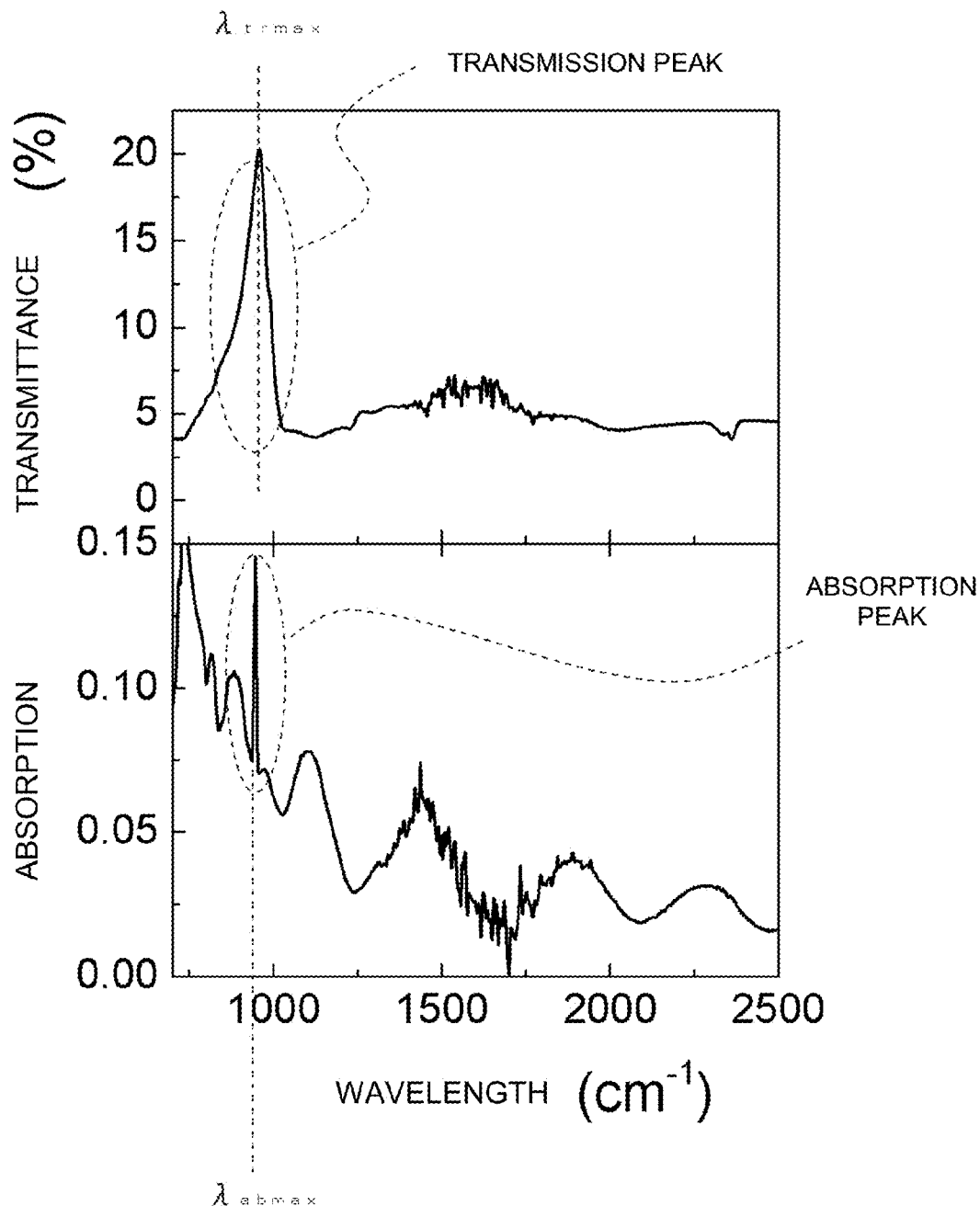
FIG. 7B is a graph illustrating a transmission spectrum of the conductive thin film of the window member incorporated into the gas detector according to the first embodiment of the present invention and an absorption spectrum of a target gas along the same wavelength axis, showing that $\lambda_{t\,r\,m\,a\,x}$ and $\lambda_{a\,b\,m\,a\,x}$ match.
Figure 8:
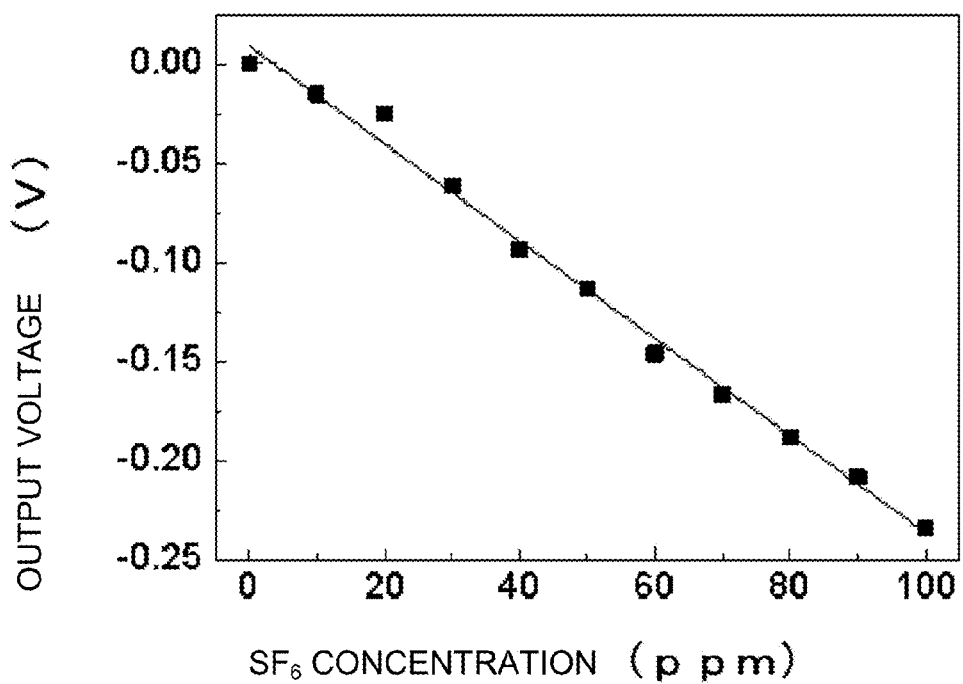
FIG. 8 is a graph illustrating the relation between a target gas concentration and an output voltage according to the first embodiment of the present invention.
Figure 9:
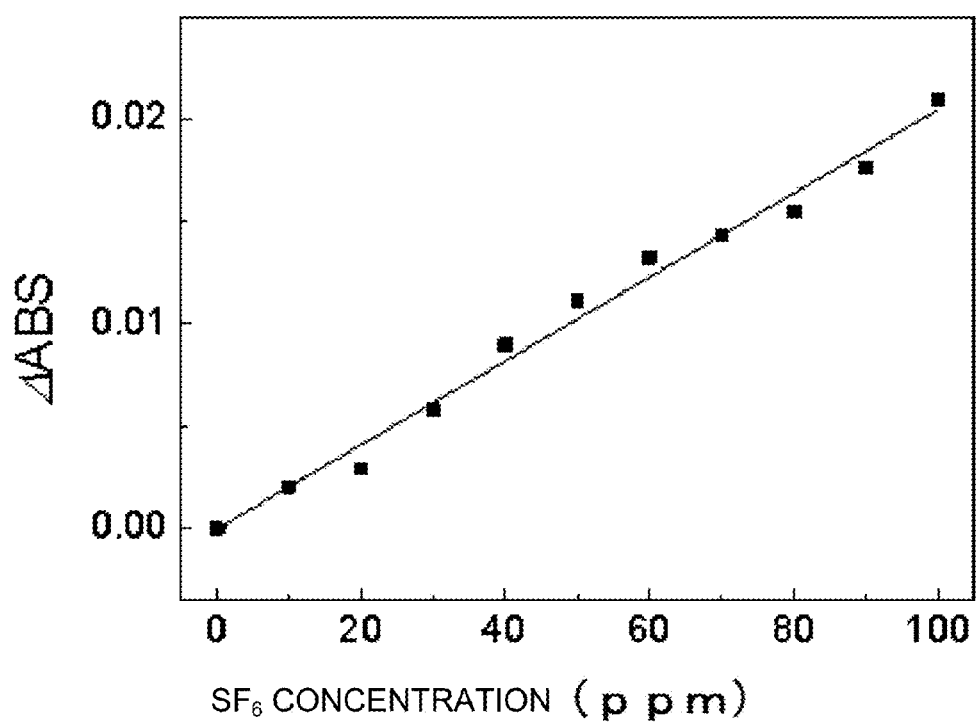
FIG. 9 is a graph illustrating the relation between a target gas concentration and changes in absorbance according to the first embodiment of the present invention.

A first embodiment will be described referring to FIGS. 1 to 9. FIG. 1 is a schematic diagram illustrating a schematic cross-sectional configuration of a gas detector. FIG. 2 is a schematic diagram illustrating the schematic configuration of a window member incorporated into the gas detector, (a) illustrating a partial and schematic upper surface configuration of the window member, and (b) illustrating a schematic cross-sectional configuration of the window member. FIG. 3 is a process diagram illustrating a method for manufacturing the window member that is incorporated into the gas detector. FIG. 4 is a photograph showing the upper surface of the window member that is incorporated into the gas detector. FIG. 5 is a graph illustrating the relation between the interval between optical apertures of an conductive thin film of the window member incorporated into the gas detector and a wavelength ($\lambda_{max}$) of the maximum transmittance at a transmission peak in a transmission spectrum. FIG. 6 is a graph illustrating a comparison between transmission spectra of respective conductive thin films for the window member incorporated into the gas detector. FIG. 7A is a graph illustrating a transmission spectrum of the conductive thin film of the window member incorporated into the gas detector and an absorption spectrum of a target gas on the same wavelength axis, which shows that the transmission spectrum and the absorption spectrum are superimposed. FIG. 7B is a graph illustrating a transmission spectrum of the conductive thin film of the window member incorporated into the gas detector and an absorption spectrum of a target gas on the same wavelength axis, which shows that $\lambda_{tr\,max}$ and $\lambda_{ab\,max}$ match. FIG. 8 is a graph illustrating the relation between a target gas concentration and an output voltage. FIG. 9 is a graph illustrating the relation between a target gas concentration and changes in absorbance.

As shown in FIG. 1A, a gas detector 10 may include a gas cell 110 that is a container defining a cell internal space 130 for a target gas; a first window member 200; a second window member 300; a light source 410; a photodetector 420; a circuit 510; and a display 520. To measure the concentration of a target gas being supplied into the cell internal space 130, the gas detector 10 may use the photodetector 420 to detect light that has been emitted from the light source 410 and has propagated through the cell internal space 130. Note that the gas detector 10 should not be limited to measure the concentration of a target gas, but may also be used to detect the presence of a target gas. The presence of a target gas may be detectable based on detecting a decrease in the light intensity of the propagated and received light. The gas detector may be configured to detect various kinds of gas.

Although sulfur hexafluoride $SF_6$ is described as an example of the target gas in the present example, the target gas should not be limited thereto, and may be another greenhouse gas such as carbon dioxide, or may be a hazardous or non-hazardous gas other than a greenhouse gas. An absorption peak in the absorption spectrum of the currently focused sulfur hexafluoride $SF_6$ exhibits a maximum absorption at 10.5 µm. The light source 410 of the present example is configured to generate near-infrared light including a wavelength of 10.5 µm in accordance with the absorption peak of sulfur hexafluoride $SF_6$. The photodetector 420 of the present example is configured to detect near-infrared light including the wavelength of 10.5 µm. Note that, if the target gas is a gas having an absorption peak in a different wavelength band, a wavelength/wavelength band of emitted light from the light source 410 and a wavelength/wavelength band that can be detected by the photodetector 420 will be adjusted in accordance therewith. That is, the disclosure of the present application should not be limited to gas detection in the near-infrared region.

The longer the cell length L110 of the gas cell 110 illustrated in FIG. 1 will be, the higher the detection sensitivity for the target gas concentration will be. Light absorption can be expressed by molecular eigenvalue×concentration×optical path length. If the concentration is decreased to 1/10, a tenfold optical path length will be required. The greater length of the gas cell 110 may be adopted to achieve higher detection sensitivity for the target gas concentration, but will result in the increased size of the gas detector 10 in accordance with the greater length. As will be apparent from the following descriptions, according to the present embodiment, it may be possible to fundamentally solve this drawback that is inherent to a method for measuring a target gas concentration according to attenuation of light, such as the "NDIR method".

The light source 410 may be configured to generate light having a wavelength belonging to an absorption peak in the absorption spectrum of the target gas. In the present example, as described above, the light source 410 generates near-infrared light. The specific configuration of the light source 410 is arbitrary, and for example the light source 410 may be a light source that generates pulsed light or a light source that may generate parallel light. A pulsed light source may be more preferable than a continuous light source because the light intensity is measured by the photodetector 420. However, a shutter might be used in combination with a continuous light source. An optical system such as a lens, a filter, a prism or a mirror may be incorporated into the light source 410, or an optical system such as a lens, a filter, a prism or a mirror may be optically coupled with the light source 410. The light source 410 may typically be a light emitting device such as an LED (light emitting diode) or an LD (laser diode), or a lamp. A wavelength of emitted light may also be adjusted by utilizing a fluorescent material. The light emitting device should not be limited to a silicon semiconductor device, and a compound semiconductor device may also be used as a light emitting device.

The photodetector 420 may be configured to detect light of a wavelength belonging to the absorption peak in the absorption spectrum of the target gas. The specific configuration of the photodetector 420 may be arbitrary. An optical system such as a lens, a filter, a prism or a mirror may be incorporated into the photodetector 420, or an optical system such as a lens, a filter, a prism or a mirror may be optically coupled with the photodetector 420. Although the photodetector 420 may typically be a compound photodiode such as InGaAs that is sensitive to light in the infrared region, the photodetector 420 should not necessarily be limited thereto, and another light-sensitive element may be utilized. It is also possible to utilize an infrared absorption-type thermosensitive element.

The light source 410 and the photodetector 420 may be arranged coaxially along an axis AX50, that is, an optical path between the light source 410 and the photodetector 420 may be a straight optical path. Accordingly, the built-in optical system in the gas detector 10 may be simplified, and simplification of assembling the product as well as lower product unit price may be achieved.

The gas cell 110 may be a hollow container into which the target gas is supplied, and a hollow gas inlet 120 and a hollow gas outlet 140 may be provided thereto. The target gas may flow into the cell internal space 130 inside the gas cell 110 via the gas inlet 120, may flow through the cell internal space 130 from the light source 410 side to the photodetector 420 side, and may be discharged to outside via the gas outlet 140. The gas cell 110, the gas inlet 120 and the gas outlet 140 are, for example, cylindrically shaped, not necessarily limited thereto though.

The window member 200 and the window member 300 may also be arranged coaxially along the axis AX50. The window member 200 may be a member that intermediates/conveys the propagation of emitted light from the light source 410 to the cell internal space 130 side. In the present example, the window member 200 is configured to be transparent to near-infrared light. The window member 200 is provided between the light source 410 and the cell internal space 130, and defines the cell internal space 130 from the light source 410 side. The window member 300 is a member that intermediates/conveys the propagation of light that has emitted from the light source 410 and has propagated through the cell internal space 130, to the photodetector 420 side. In the present example the window member 300 is configured to be transparent to near-infrared light. The window member 300 is provided between the cell internal space 130 and the photodetector 420, and defines the cell internal space 130 from the photodetector 420 side. The front view shape of the window members 200 and 300 is arbitrary, and for example is a disc shape or a rectangular shape.

The interval between the window member 200 and the window member 300 may indicate the cell length L110 of the gas cell 110 according to the present example. In the present example, although depicted as being long in FIG. 1, the cell length L110 is evidently shorter than the conventional products, and sufficient detection sensitivity for the target gas concentration can be secured even with a length of several centimeters thereof. According to a simulation performed by the present inventor, the cell length L110 of the gas cell 110 can be shortened to around 10 microns. Accordingly, miniaturization of the gas detector 10 may be envisaged by utilizing a MEMS (micro electro mechanical systems) or the like.

FIG. 2 is a schematic diagram illustrating the schematic configuration of the window member 200 incorporated into the gas detector 10, (a) illustrating a partial and schematic upper surface configuration of the window member 200, and (b) illustrating a schematic cross-sectional configuration of the window member 200. Note that the configuration of the window member 300 is substantially identical with that of the window member 200, and hence redundant descriptions shall be omitted herein.

As shown in FIG. 2, the window member 200 is an optical component in which an electrically conductive thin film 220 is provided on a support substrate 210, and a plurality of optical apertures 222 are regularly and two-dimensionally arranged in the conductive thin film 220. The support substrate 210 has a first main surface 211 at a side being exposed to the cell internal space 130, and a second main surface 212 at a side facing the light source 410. The first main surface 211 and the second main surface 212 are flat surfaces arranged in parallel one another, and the substrate thickness of the support substrate 210 is defined by these main surfaces. The first main surface 211 is also a light emission surface of the window member 200, while the second main surface 212 is also a light incidence surface of the window member 200.

The conductive thin film 220 is formed on the first main surface 211 of the support substrate 210. The conductive thin film 220 is contactable with the target gas in the cell internal space 130, and the conductive thin film 220 is also provided on the optical path between the light source 410 and the photodetector 420.

The support substrate 210 is a support substrate of the conductive thin film 220 and is transparent to the emitted light from the light source 410. In the present example, the support substrate 210 is transparent to near-infrared light. An arbitrary material can be used as the material of the support substrate 210 as long as the material has transparency for the light belonging to an absorption peak in the absorption spectrum of the target gas. In the present example, the support substrate 210 is a silicon substrate with a thickness of 450 to 550 μm. Since more near-infrared light will be absorbed if the thickness of the silicon substrate increases, it may be desirable to make the silicon substrate thin not to promote such absorption of near-infrared light. Preferably, the thickness of the silicon substrate is 200 to 1000 μm. Another substrate made of germanium, sapphire or calcium fluoride or the like may also be useable.

The conductive thin film 220 is a thin film made of an electrically conductive material that is exemplified by a metal, and the optical apertures 222 are regularly provided. The conductive thin film 220 is typically made of a material selected from the group consisting of silver, gold, copper, chromium, aluminum, iron, titanium, nickel, cobalt, rhodium, palladium, platinum, iridium, ruthenium, osmium, zinc, and rhenium. The thickness of the conductive thin film 220 is preferably 50 nm to 100 nm. Each optical aperture 222 is typically a space formed by partially removing the conductive thin film 220, but it may possibly filled with a transparent material. The arrangement interval of the optical apertures 222 can be changed depending on an absorption peak in the absorption spectrum of the target gas. The aperture diameter or maximum aperture width of the optical aperture 222 can be changed depending on the absorption peak in the absorption spectrum of the target gas. The shape of the optical apertures 222 should not be limited to the circular shape illustrated in the drawings.

A transmission peak in the transmission spectrum of the conductive thin film 220 is adjusted by regularly providing the optical aperture 222. A transmission peak in the transmission spectrum of the conductive thin film can be explained by reference to an "anomalous transmission phenomenon". The "anomalous transmission phenomenon" is a phenomenon whereby an anomalous transmission peak appears in a transmission spectrum due to resonant coupling between incident light and surface plasmon polaritons (SPPs) on the surface of an electrically conductive member in which a periodic structure of regular apertures is provided. As will be apparent from the following descriptions, the studies by the inventor of the present application has revealed that by superimposing the transmission peak in the transmission spectrum of the conductive thin film 220 over the absorption peak in the absorption spectrum of the target gas along a wavelength axis, an adequate detection sensitivity for the target gas may be secured despite that the cell length L110 was shortened. This may be because the target gas and the emitted light of the light source 410 greatly interact at the surface of the conductive thin film 220 where the SPPs are excited, particularly at the edges of the optical apertures 222, in other words, the target gas absorbs a greater amount of the emitted light from the light source 410.

Because the interval between the optical apertures 222 influences the transmission peak in the transmission spectrum of the conductive thin film 220, it may be preferable to arrange the optical apertures 222 not in a four-sided lattice shape, but rather in a triangular lattice shape in which the interval between adjacent optical apertures 222 is set to be equal in plane. For example, in a case where the optical apertures 222 are adjacent in a four-sided lattice shape, two transmission peaks will appear in the transmission spectrum of the conductive thin film 220 because the length of a diagonal line is longer than the length of each side in the square shape. This drawback may be eliminated by making the interval between adjacent optical apertures 222 equal in plane.

Referring to FIG. 2(a), when FIG. 2 is viewed in front, there is an array L1 of optical apertures 222 arranged at a constant interval W7 in the transverse direction (first direction) (optical aperture array) and an array L2 of optical apertures 222 arranged at the constant interval W7 in the same transverse direction (optical aperture array). The array L1 and array L2 are adjacent in the vertical direction (second direction) when FIG. 2 is viewed in front. It will be understood that the optical apertures 222 of the array L2 are shifted in the rightward direction by an amount corresponding to W7/2 relative to the optical apertures 222 of the array L1 when FIG. 2 is viewed in front.

The respective optical apertures 222 may be arranged at the respective vertices of respective triangular lattices, that is, equilateral triangles, and the intervals between adjacent optical apertures 222 are made uniform at the interval W7. In other words, the optical apertures 222 may be arranged in a zig-zag shape between the array L1 and the array L2. This also applies for the other arrays such as an array L3 and an array L4. For example, the interval between the diagonally arranged adjacent optical apertures 222 in the arrays L3 and L4 has the interval W7 either. Note that the aforementioned first and second directions are orthogonal one another, and a plane where the conductive thin film 220 exists is defined by these directions.

Any method for manufacturing the window member 200 may be adoptable. For example, the window member 200 may be manufactured based on a photolithography technique as shown in FIG. 3. As shown in FIG. 3, a sacrificial layer 230 made of, for example, a resist may be formed on the support substrate 210 (see (a) in FIG. 3); patterning of the sacrificial layer 230 may be then performed by selective light exposure and washing (see (b) in FIG. 3); a conductive layer 220' to be the conductive thin film 220 may be then formed on the patterned sacrificial layer 230 (see (c) in FIG. 3); and thereafter the sacrificial layer 230 on which the conductive layer 220' is deposited may be removed from the top of the support substrate 210 (see (d) in FIG. 3) to thereby obtain the window member 200 shown in FIG. 2. Note that laser processing or the like may be utilized instead of photolithography technology.

FIG. 4 shows an enlarged photograph of the conductive thin film 220 of the window member 200.

FIG. 5 is a graph illustrating the relation between the interval between the optical apertures 222 of the conductive thin film 220 of the window member 200 incorporated into the gas detector 10 and a wavelength ($\lambda_{max}$) of the maximum transmittance at a transmission peak in the transmission spectrum. FIG. 6 is a graph illustrating a comparison between transmission spectra of respective conductive thin films for the window member 200 incorporated into the gas detector 10. FIG. 5 shows results in a case where eight window member samples were used, and in which eight plots are approximated by a straight line. FIG. 6 illustrates the respective transmission spectra of the eight samples that relate to FIG. 5.

As shown in FIG. 5, the wavelength $\lambda_{max}$ shifts to the longer wavelength side as the interval between the optical apertures 222 increases, that is, the transmission peak in the transmission spectrum of the conductive thin film 220 shifts to the longer wavelength side. The interval between the optical apertures 222 explained herein indicates, for example, the interval W7 shown in FIG. 2. It is understandable that an interval adjustment at the μm level causes a shift of the maximum intensity wavelength at the μm level.

As shown in FIG. 6, it is recognizable that the window member of each sample has a single transmission peak for a transmittance in a band from visible red to near infrared (650 nm to 1150 nm).

FIGS. 7A and 7B are graphs in which a transmission spectrum of a conductive thin film at the window member incorporated into the gas detector and an absorption spectrum of the target gas are shown along the same wavelength axis. In the present embodiment, as shown in FIGS. 7A and 7B, the transmission peak in the transmission spectrum of the conductive thin film 220 is superimposed over an absorption peak in the absorption spectrum of the target gas along the wavelength axis. In other words, the wavelength band of the transmission peak in the transmission spectrum of the conductive thin film 220 and the wavelength band of the absorption peak in the absorption spectrum of the target gas overlap, that is, include a common wavelength band. The studies and simulation results made and obtained by the inventor of the present application has revealed that, such a feature may promote the absorption of near-infrared light by the target gas in the vicinity of the conductive thin film, more specifically, and without any intention to limit the present invention, in the vicinity of side faces defining the optical apertures of the conductive thin film and in the vicinity of the surface of the first main surface of the conductive thin film at the side being exposed to the target gas so that an adequate detection sensitivity may be secured despite that the cell length L110 is shortened.

In the case illustrated in FIG. 7A, a wavelength $\lambda_{ab\,max}$ at which the maximum absorption of the absorption peak in the absorption spectrum of the target gas occurs is 10.5 μm, and a wavelength $\lambda_{tr\,max}$ at which the maximum transmittance at the transmission peak in the transmission spectrum of the conductive thin film 220 occurs is 10.46 μm. Thus, even when there is a difference between the wavelength $\lambda_{ab\,max}$ and the wavelength $\lambda_{tr\,max}$, it may be sufficient as long as overlapping of the transmission peak and the absorption peak is secured.

For example, when the wavelength at which the maximum absorption of the absorption peak in the absorption spectrum of the target gas occurs is taken as $\lambda_{ab\,max}$ and the wavelength at which the maximum transmittance at the transmission peak in the transmission spectrum of the conductive thin film is taken as $\lambda_{tr\,max}$, $\lambda_{ab\,max} \times 0.8 \leq \lambda_{tr\,max} \leq \lambda_{ab\,max} \times 1.2$ may be satisfied, preferably $\lambda_{ab\,max} \times 0.9 \leq \lambda_{tr\,max} \leq \lambda_{ab\,max} \times 1.1$ may be satisfied, and more preferably $\lambda_{ab\,max} \times 0.95 \leq \lambda_{tr\,max} \leq \lambda_{ab\,max} \times 1.05$ may be satisfied. In cases where such conditions were satisfied, adequate overlapping between the transmission peak in the transmission spectrum and the absorption peak in the absorption spectrum may be secured.

In the case illustrated in FIG. 7B, the wavelength $\lambda_{ab\,max}$ at which the maximum absorption of the absorption peak in the absorption spectrum of the target gas occurs is 10.5 μm, and the wavelength $\lambda_{tr\,max}$ at which the maximum transmittance at the transmission peak in the transmission spectrum of the conductive thin film 220 occurs is 10.5 μm. It may be desirable that $\lambda_{ab\,max}$ and $\lambda_{tr\,max}$ completely match in this manner. In the case illustrated in FIG. 7B, the wavelength bandwidth of the absorption peak is sufficiently narrower than the wavelength bandwidth of the transmission peak, and the absorption peak is completely enclosed inside the wavelength bandwidth of the transmission peak. When a mixed gas that includes two or more kinds of gases is adopted as the target gas, it is also conceivable that the wavelength bandwidth of the absorption peak will be wider than the wavelength bandwidth of the transmission peak.

FIG. 8 illustrates that, in a case where $SF_6$ is used as the target gas under the present configuration, the voltage output changes linearly in accordance with an increase in the concentration of the target gas. FIG. 9 illustrates that, likewise, in a case where $SF_6$ is used as the target gas under the present configuration, a change in the absorbance (ΔABS) changes linearly in accordance with an increase in the concentration of the target gas. It is understandable that fluctuations in the ppm level of the target gas concentration of the target gas can also be accurately detected.

The photodetector 420 shown in FIG. 1 typically includes a light detecting element such as a photodiode, an analog peripheral circuit that is electrically coupled to the light detecting element, and as an option, an A/D conversion circuit that converts an analog signal to a digital signal or the like. An output signal of the photodetector 420 shows the intensity of light detected by the photodetector 420. The circuit 510 includes an analog or digital circuit that processes output signals of the photodetector 420, and depending on the case, is comprised of a computer including a CPU or a memory. The circuit 510 determines and outputs a gas concentration value corresponding to the intensity of the aforementioned detected light based on an output signal of the photodetector 420. The output signal of the circuit 510 is transmitted to the display 520, and the display 520 displays the gas concentration value. The relation between the intensity of detected light and a gas concentration value may be experimentally determined in advance, and the correlation may be determined by utilizing a predetermined arithmetic expression or a look-up table.

Operation of the gas detector 10 will now be described. The target gas is supplied into the cell internal space 130 of the gas cell 110 through the gas inlet 120, and is discharged through the gas outlet 140. When the light source 410 emits near-infrared pulsed light, the near-infrared pulsed light is transmitted through the support substrate 210 of the window member 200, is transmitted through the conductive thin film 220, passes through the cell internal space 130, is transmitted through an conductive thin film 320 of the window member 300, and is transmitted through a support substrate 310 of the window member 300 to be incident on the photodetector 420. A predetermined proportion of the near-infrared pulsed light is absorbed by the support substrate of the respective window members. A predetermined proportion of the near-infrared pulsed light is reflected by the conductive thin film of the respective window members. A proportion of the near-infrared pulsed light that is in accordance with the amount/concentration of the target gas that is present in the cell internal space 130 of the gas cell 110 is absorbed by the target gas.

The photodetector 420 detects the intensity of near-infrared light based on the amount of photoelectric current generated in the photodiode. The photodetector 420 converts the photoelectric current to a voltage and outputs to the circuit 510 a detection voltage having a magnitude reflecting the amount of photoelectric current. The circuit 510 processes the detection voltage and, for example, determines a target gas concentration value based on the detection voltage and outputs the target gas concentration value. Those skilled in the art will understand that the relation between a detection voltage value and a target gas concentration value can be experimentally determined beforehand (see FIG. 8). The display 520 displays the target gas concentration value transmitted from the circuit 510.

In the present embodiment, since the conductive thin films 220 and 320 in which the periodic structures of the optical apertures 222 are provided are provided on the optical path so as to come in contact with the target gas, and adequate light absorption by the target gas can be promoted in the vicinity of the conductive thin film 220, adequate detection sensitivity for the target gas can be secured without highly depending on the cell length L110 of the gas cell 110. Accordingly, even when the cell length L110 of the gas cell 110 shown in FIG. 1 is greatly shortened than before, adequate detection sensitivity for the target gas may be secured. For example, a gas cell based on the existing NDIR method required that a length of "20 cm" or more should be secured as the length of a target gas flow path for detecting a 100 ppm target gas. In the present embodiment, the cell length L110 of the gas cell 110 required to secure the same degree of sensitivity is "2 cm," and thus ¹⁄₁₀ downsizing compared to the existing method may be achieved.

In addition, according to the present embodiment, a plurality of conductive thin films, two in the present example, namely, the conductive thin films 220 and 320, are provided on the optical path from the light source 410 to the photodetector 420. Accordingly, an interaction region between conductive thin films and target gas may be adequately secured, and adequate detection sensitivity for the target gas concentration can be secured. The number of conductive thin films arranged on the optical path is arbitrary, and two or more, for example, four or eight conductive thin films may be provided to secure the detection sensitivity. Note that an adverse effect of a decrease in transmittance may be avoided by making the number of conductive thin film eight or less. It will be apparent from the foregoing descriptions and from FIGS. 7A and 7B that the overall transmittance is decreased by increasing the number of conductive thin films. Naturally, only one conductive thin film may be used.

It is not essential to provide a conductive thin film at the window member, and a conductive thin film may be provided at another location on the optical path between the light source 410 and the photodetector 420. For example, an optical component having the same composition as the window member 200 and window member 300 may be provided as an intermediate element between the window member 200 and window member 300. That is, the window member is merely one example of an optical component.

[Second Embodiment]

Figure 10:
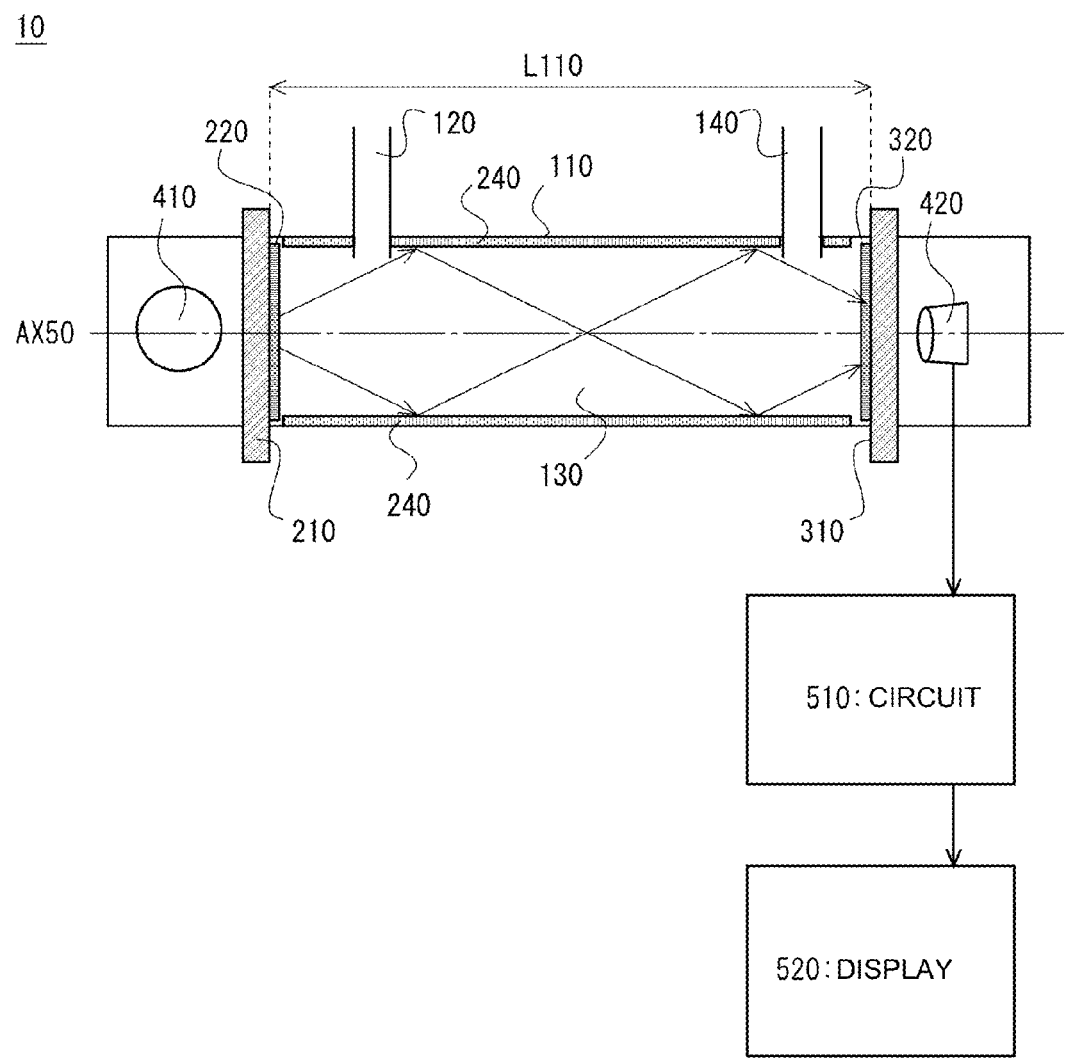
FIG. 10 is a schematic diagram illustrating a schematic cross-sectional configuration of a gas detector according to a second embodiment of the present invention.

A second embodiment will now be described referring to FIG. 10. FIG. 10 is a schematic diagram illustrating a schematic cross-sectional configuration of a gas detector. In the present embodiment, a conductive thin film that is identical with the conductive thin film described in the first embodiment is provided on an inner side of the gas cell 110 and is arranged on the optical path from the light source 410 to the photodetector 420. Accordingly, a more adequate interaction area can be secured between the conductive thin film and the target gas. Similar advantageous effects as those in the first embodiment may be obtained in the present embodiment case either.

As shown in FIG. 10, a conductive thin film 240 that is identical with the conductive thin film described in the first embodiment is provided on a reflective inner side of the gas cell 110. Emitted light from the light source 410 diverges in the course of propagating along the optical path, and is reflected by the conductive thin film 240 on the inner side of the gas cell 110 and is also transmitted there-through and reflected by the reflective inner side. The inner side of the gas cell 110 has adequate reflectivity, and transmission of incident light through the gas cell 110 itself is inhibited. In the present embodiment also, a transmission peak in the transmission spectrum of the conductive thin film 240 is superimposed over an absorption peak in the absorption spectrum of the target gas. Accordingly, absorption of near-infrared light by the target gas is promoted in the vicinity of the conductive thin film 240, and adequate detection sensitivity for the target gas may be secured regardless that the cell length L110 of the gas cell 110 is shortened.

[Third Embodiment]

Figure 11:
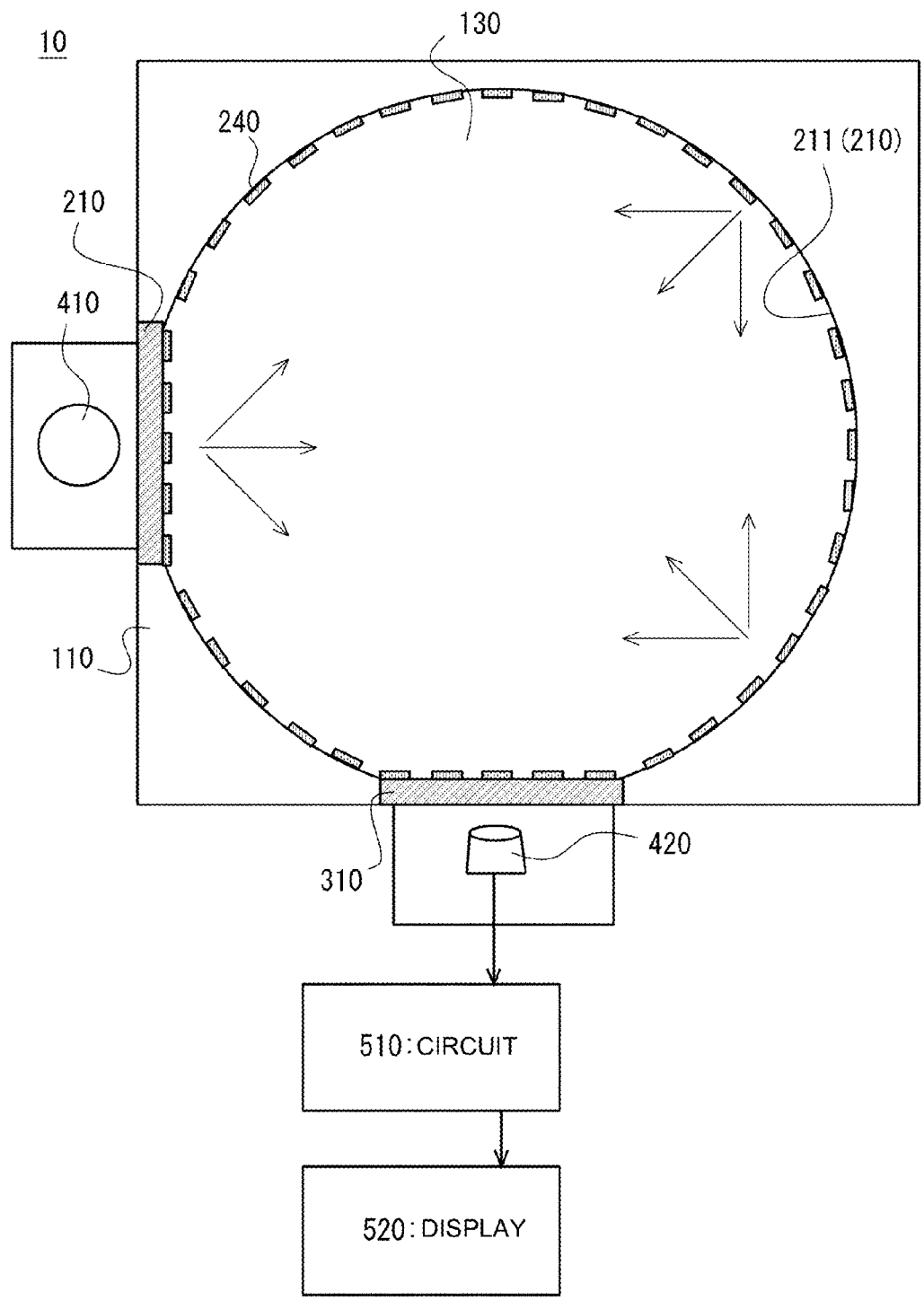
FIG. 11 is a schematic diagram illustrating a schematic cross-sectional configuration of a gas detector according to a third embodiment of the present invention.

A third embodiment will now be described referring to FIG. 11. FIG. 11 is a schematic diagram illustrating a schematic cross-sectional configuration of a gas detector. In the present embodiment, the gas cell 110 has a spherical reflective inner side like an integrating sphere, and a conductive thin film that is identical with the conductive thin film described in the first embodiment is provided on a reflective spherical surface of the gas cell 110. The conductive thin film is arranged on the optical path from the light source 410 to the photodetector 420. A more adequate interaction area may be secured between the conductive thin film and the target gas. Similar advantageous effects as those in the first embodiment may be obtained in the present embodiment case either.

As shown in FIG. 11, the gas cell 110 is constructed to have a hollow cell internal space 130, and the cell internal space 130 is defined by the spherical surface. Note that a target gas inlet and a target gas outlet that are not shown in the drawing are communicated to the cell internal space 130 inside the gas cell 110. As shown schematically by arrows in FIG. 11, inside the gas cell 110 the emitted light from the light source 410 is reflected by the conductive thin film 240 and is also transmitted there-through and is reflected by the reflective inner side of the gas cell 110. The inner side of the gas cell 110 is equipped with adequate reflectivity, and transmission of incident light through the gas cell 110 itself is inhibited. The constituent material of the gas cell 110 is, for example, one or more silicon substrates. For example, a hollow spherical space may be formed by causing hemispheric cavities formed in two flat silicon substrates to face each other.

[Fourth Embodiment]

Figure 12:
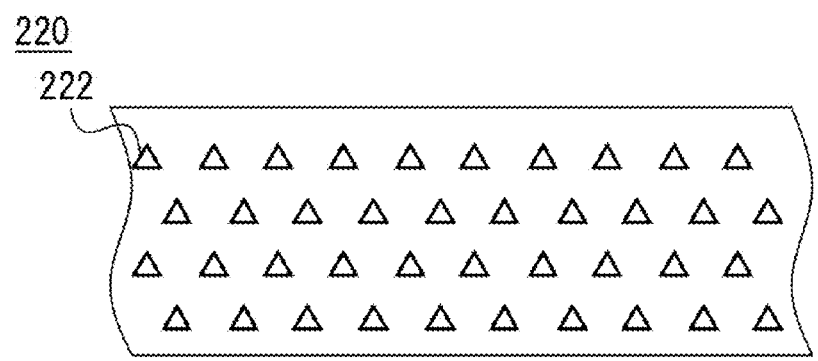
FIG. 12 is a schematic diagram illustrating a partial and schematic upper surface configuration of window member that is incorporated into a gas detector according to a fourth embodiment of the present invention.

A fourth embodiment will now be described referring to FIG. 12. FIG. 12 is a schematic diagram illustrating a partial and schematic upper surface configuration of a window member incorporated into a gas detector. Although in the above described embodiments the shape of the optical apertures provided in the conductive thin film is circular, the aperture shape may be polygonal. In a case of a polygonal shape, it is predicted that interaction between emitted light from the light source 410 and target gas will be adequately promoted at the edges of the optical apertures because of an optical edge effect whereby light is liable to localize at the edges. Similar advantageous effects as in the first embodiment may be obtained in the present embodiment case either. Further, in comparison to a case where circular optical apertures are provided in the conductive thin film, it is expected that interaction between target gas and light will occur more adequately in the vicinity of the conductive thin film.

As shown in FIG. 12, triangular optical apertures 222 as one example of polygonal optical apertures are provided in the conductive thin film 220. In other respects, the fourth embodiment is the same as the first embodiment. The optical apertures 222 may also be a square shape, a pentagonal shape, a hexagonal shape or the like, and should not be limited to a triangular shape.

EXAMPLES

Figure 13:
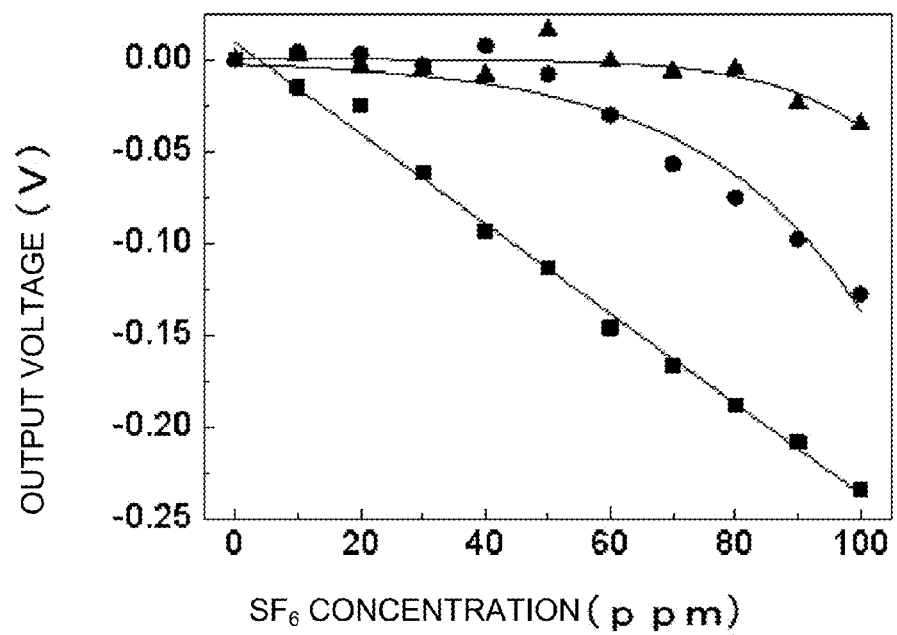
FIG. 13 is a graph illustrating a comparison between examples of the present invention and a comparative example.
Figure 14:
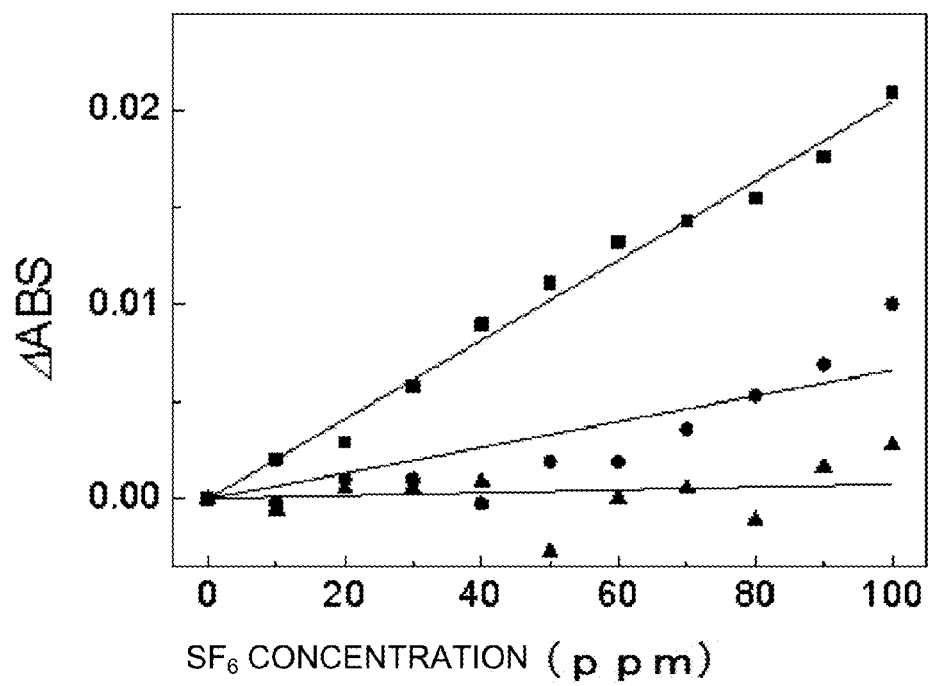
FIG. 14 is a graph illustrating comparison between examples of the present invention and a comparative example.

FIGS. 13 and 14 are graphs each illustrating a comparison between inventive examples and a comparative example. The symbol ■ indicates an evaluation result of an example having an identical configuration with FIG. 1, and this example is referred to as "Example 1". The symbol ● indicates an evaluation result of an example in which one of the two conductive thin films is provided at a side not to contact the target gas in the configuration of FIG. 1, and this example is referred to as "Example 2". The symbol ▲ indicates an evaluation result of a comparative example in which both of the conductive thin films are respectively provided at a side not to contact the target gas.

In the case of Example 1, the target gas was detected from 5 ppm. In the case of Example 2, the target gas was detected from 50 ppm. In the case of the comparative example, the target gas was detected from 80 ppm. The significance of exposing the conductive thin films to the target gas was thus confirmed. Further, the significance of adequately securing an interaction area between the conductive thin film and the target gas was confirmed.

Note that the used target gas was sulfur hexafluoride as described in the first embodiment. The cell length was 2 cm. A gas mixing apparatus was communicated to the gas inlet 120. A nitrogen cylinder and a target gas cylinder in which nitrogen and sulfur hexafluoride were mixed were connected to the gas mixing apparatus. The voltage output of the photodetector 420 was supplied to an oscilloscope, and a change in the output voltage was monitored. The required electric power was supplied to the light source, the photodetector and the oscilloscope from an electric power source.

Based on the above teachings, various modifications may be added to the respective embodiments by those skilled in the art. A member in which the conductive thin film is provided should not be limited to a window member, and the conductive thin films may be provided at other locations on the optical path.

It will be apparent from the above descriptions that the following gas detection method is also disclosed in the present application. An exemplary gas detection method disclosed in the present application includes: a step of irradiating, to an conductive thin film provided in a space to which a target gas having an absorption peak in an absorption spectrum is supplied, light having at least a wavelength belonging to the absorption peak, a plurality of optical apertures being regularly arranged in the conductive thin film such that a transmission peak in a transmission spectrum is superimposed over the absorption peak in the absorption spectrum along a wavelength axis; and a step of detecting light that has propagated across the space through the conductive thin film.

Figure 15:
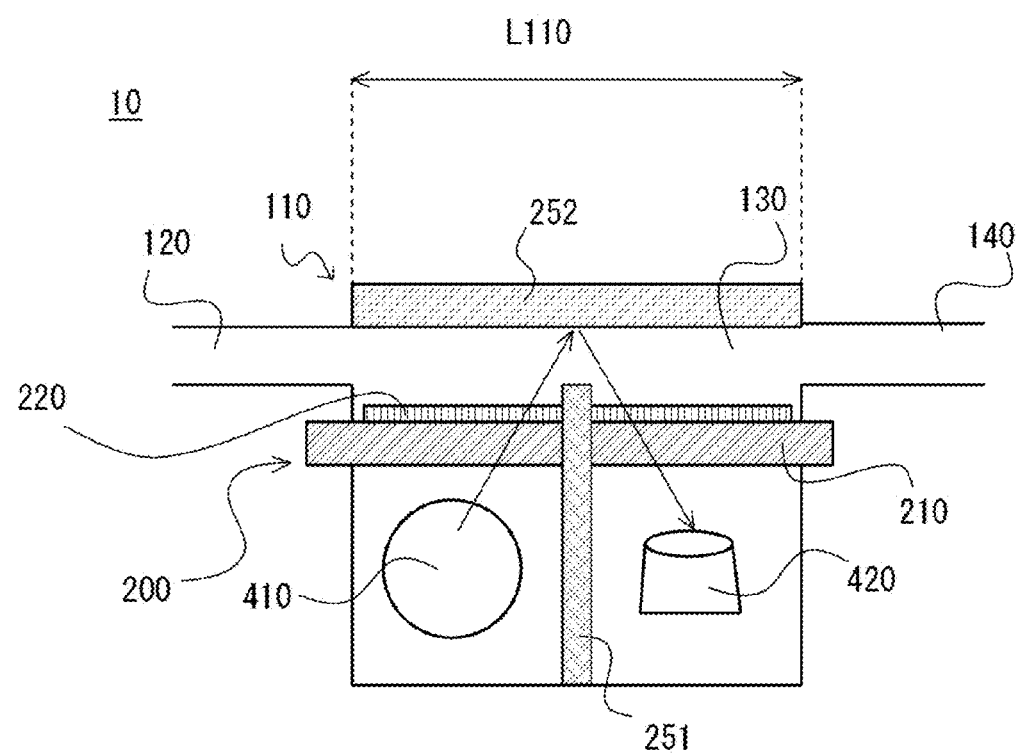
FIG. 15 is a schematic diagram illustrating a modification of an embodiment of the present invention.

As shown in FIG. 15, the light source 410 and the photodetector 420 may be provided at the same side. In this case, as shown in FIG. 15, a light shield 251 may preferably be provided for inhibiting incidence of emitted light from the light source 410 onto the photodetector 420 without passing though the cell internal space 130. For example, an opening is formed in the window member 200 by dicing, and the light shading unit is inserted into the opening. A reflector 252 is provided facing the window member 200, and accordingly emitted light from the light source 410 that has propagated through the cell internal space 130 can travel towards the photodetector 420. An optical component having the same structure as the window member 200 may be arranged instead of the reflection member 252. In such a case the conductive thin film on the substrate functions as a reflective layer, and interaction between the target gas and light may be promoted. It is preferable to set a V-shaped optical path as indicated by arrows in FIG. 15. In the case illustrated in FIG. 15, the gas detector 10 can be noticeably miniaturized. Light receiving/emitting devices in which a light receiving device and a light emitting device are integrated have been widely used, and an apparatus may be configured utilizing such light receiving/emitting devices. An ultimate integration may be achieved by utilizing a semiconductor process whereby a light receiving device and a light emitting device of semiconductor layered products are provided onto a common substrate of the support substrate 210.

REFERENCE SIGNS LIST

10 Gas detector
110 Gas cell
120 Gas inlet
130 Cell internal space
140 Gas outlet
200 Window member
210 Support substrate
220 Electrically conductive thin film
300 Window member
310 Support substrate
320 Electrically conductive thin film
410 Light source
420 Photodetector
510 Circuit
520 Display

The invention claimed is:

1. A gas detector, comprising:
a space into which a target gas is supplied, the target gas exhibiting an absorption peak in an absorption spectrum;
a light source configured to generate light having at least a wavelength belonging to the absorption peak;
a photodetector configured to detect the light that has emitted from the light source and has propagated through the space;
a conductive thin film on which surface plasmon polaritons are excited in response to the light from the light source and in which a plurality of optical apertures are regularly arranged such that a transmission peak in a transmission spectrum is superimposed over the absorption peak in the absorption spectrum along a wavelength axis, the transmission peak being in accordance with an interval of the regularly arranged optical apertures, the conductive thin film being able to transmit light corresponding to the transmission peak;
a window member that intermediates propagation of the emitted light from the light source to the space, or that intermediates propagation of the light that has propagated through the space to the photodetector,
wherein the conductive thin film is provided on the window member that is arranged on an optical path extending from the light source to the photodetector, and is provided so as to be contactable with the target gas within the space.

2. The gas detector of claim 1, wherein the plurality of optical apertures are two-dimensionally arranged at a predetermined interval along first and second directions that are orthogonal one another in a plane where the conductive thin film exists.

3. The gas detector of claim 2, wherein the plurality of optical apertures include a first and second optical aperture arrays in which the optical apertures are arranged along the first direction, the second optical aperture array being arranged adjacent to the first optical aperture array in the second direction, and arrangement positions of the optical apertures in the second optical aperture array being shifted in the first direction by an amount corresponding to a value of half of the predetermined interval relative to arrangement positions of the optical apertures in the first optical aperture array.

4. The gas detector of claim 2, wherein an interval between the adjacent optical apertures in the optical aperture array in which the optical apertures are arranged along the first direction and an interval between the optical aperture in said optical aperture array and the optical aperture in another optical aperture array adjacent thereto in a diagonal direction are equal.

5. The gas detector of claim 1 wherein the plurality of optical apertures are respectively provided at positions each corresponding to a vertex in a triangular shape that is a unit of a triangular lattice.

6. The gas detector of claim 1, wherein the conductive thin film is selected from a group consisting of silver, gold, copper, chromium, aluminum, iron, titanium, nickel, cobalt, rhodium, palladium, platinum, iridium, ruthenium, osmium, zinc, and rhenium.

7. The gas detector of claim 1, wherein the space is defined by a gas cell having a gas inlet and a gas outlet.

8. The gas detector of claim 1 wherein the space is defined by a gas cell having a gas inlet and a gas outlet, and the conductive thin film is provided on a reflective inner side of the gas cell.

9. The gas detector of claim 1, wherein the space is defined by a reflective spherical surface, and the conductive thin film is provided on the spherical surface.

* * * * *